(12) United States Patent
Córdova et al.

(10) Patent No.: US 10,287,226 B2
(45) Date of Patent: May 14, 2019

(54) MILD CATALYTIC REDUCTION OF C—O BONDS AND C═O BONDS USING A RECYCLABLE CATALYST SYSTEM

(71) Applicant: ORGANOFUEL SWEDEN AB, Sundsvall (SE)

(72) Inventors: Armando Córdova, Stockholm (SE); Samson Afewerki, Uppsala (SE); Carlos Palo-Nieto, Bristol (GB)

(73) Assignee: ORGANOFUEL SWEDEN AB, Sundsvall (SE)

( * ) Notice: Subject to any disclaimer, the term of this patent is extended or adjusted under 35 U.S.C. 154(b) by 0 days.

(21) Appl. No.: 15/522,838

(22) PCT Filed: Oct. 30, 2015

(86) PCT No.: PCT/EP2015/075333
§ 371 (c)(1),
(2) Date: Apr. 28, 2017

(87) PCT Pub. No.: WO2016/066835
PCT Pub. Date: May 6, 2016

(65) Prior Publication Data
US 2017/0334819 A1 Nov. 23, 2017

Related U.S. Application Data

(60) Provisional application No. 62/072,774, filed on Oct. 30, 2014.

(51) Int. Cl.
| | | |
|---|---|---|
| C07C 41/18 | (2006.01) | |
| C07C 29/145 | (2006.01) | |
| C07C 41/26 | (2006.01) | |
| C07C 209/32 | (2006.01) | |
| C07C 209/68 | (2006.01) | |
| C07C 45/30 | (2006.01) | |
| C07C 45/51 | (2006.01) | |
| C10G 3/00 | (2006.01) | |
| C07C 1/22 | (2006.01) | |
| C07C 43/205 | (2006.01) | |
| C07C 43/23 | (2006.01) | |
| C07C 47/575 | (2006.01) | |
| C07C 209/36 | (2006.01) | |
| C07C 211/45 | (2006.01) | |
| C10L 1/02 | (2006.01) | |
| C10L 1/04 | (2006.01) | |

(52) U.S. Cl.
CPC ............ *C07C 41/18* (2013.01); *C07C 1/22* (2013.01); *C07C 29/145* (2013.01); *C07C 41/26* (2013.01); *C07C 43/205* (2013.01); *C07C 43/23* (2013.01); *C07C 45/30* (2013.01); *C07C 45/512* (2013.01); *C07C 47/575* (2013.01); *C07C 209/325* (2013.01); *C07C 209/36* (2013.01); *C07C 209/68* (2013.01); *C07C 211/45* (2013.01); *C10G 3/45* (2013.01); *C10G 3/47* (2013.01); *C10L 1/02* (2013.01); *C10L 1/04* (2013.01); *C07C 2521/08* (2013.01); *C07C 2523/44* (2013.01); *C07C 2531/12* (2013.01); *C10L 2200/04* (2013.01); *Y02P 20/52* (2015.11); *Y02P 20/584* (2015.11); *Y02P 30/20* (2015.11)

(58) Field of Classification Search
None
See application file for complete search history.

(56) References Cited

U.S. PATENT DOCUMENTS 4,421,938 A 12/1983 Windawi

FOREIGN PATENT DOCUMENTS

CN 101564692 * 6/2009 ............. B01J 23/89

OTHER PUBLICATIONS

Derwent Abstract of CN101564692, 2009, 4 pages.*
L.B. Belykh, et al., "Hydrogenation Catalysts Based on Palladium Bisacetylacetonate and Lithium Tetrahydroaluminate: Formation Mechanism and Reasons for Modified Effect of Water," Russian Journal of Applied Chemistry, 2008, vol. 81, No. 6, pp. 956-964.
Jian Feng, et al., "Catalytic transfer hydrogenolysis of α-methylbenzyl alcohol using palladium catalysts and formic acid," Applied Catalysis A: General, 354 (2009) pp. 38-43.
Cho Rim Lee, et al., "Catalytic roles of metals and supports on hydrodeoxygenation of lignin monomer guaiacol," Catalysis Communications 17 (2012) pp. 54-58.
Masaki Okamoto, et al., "Polymers as novel modifiers for supported metal catalyst in hydrogenation of benzaldehydes," Journal of Catalysis 276 (2010) pp. 423-428.
Sheldon G. Shore, et al., "Vapor phase hydrogenation of phenol over silica supported Pd and Pd-Yb catalysts," Catalysis Communications 3 (2002) pp. 77-84.
Nakul Thakar, et al., "Deuteration study to elucidate hydrogenolysis of benzylic alcohols over supported palladium catalysts," Journal of Catalysis 246 (2007) pp. 344-350.
Oscar Verho, et al., "Mild and Selective Hydrogenation of Nitro Compounds using Palladium Nanoparticles Supported on Amino-Functionalized Mesocellular Foam," CHEMCATCHEM, vol. 6, 2014, pp. 3153-3159.
Office Action From Europe Application No. 15 794 108.9 dated Oct. 2, 2018.

* cited by examiner

*Primary Examiner* — Clinton A Brooks
(74) *Attorney, Agent, or Firm* — Whitmyer IP Group LLC

(57) ABSTRACT

A method of reducing a C—O bond to the corresponding C—H bond in a substrate, which could be a benzylic alcohol, allylic alcohol, ester or an ether bond beta to a hydroxyl group or alpha to a carbonyl group using a recyclable metal catalyst system. The recyclable catalyst system is also applicable to reducing a C═O bond to the corresponding C—OH bond and then C—H bond. These methodologies can be linked in one-pot to selective oxidation and depolymerizations of aromatic polyols such as lignin.

21 Claims, No Drawings

MILD CATALYTIC REDUCTION OF C—O BONDS AND C=O BONDS USING A RECYCLABLE CATALYST SYSTEM

CROSS-REFERENCE TO PRIOR APPLICATIONS

This application is a § 371 National Stage Application of PCT International Application No. PCT/EP2015/075333 filed Oct. 30, 2015, which claims priority to U.S. Provisional Application No. 62/072,774 filed Oct. 30, 2014, each of which are herein incorporated by reference in their entirety.

FIELD OF INVENTION

The present invention relates to eco-friendly methodology for the conversion of alcohols to hydrocarbons as well as conversion of carbonyls such as aldehydes and ketones to alcohols and then hydrocarbons

BACKGROUND

Alcohols are versatile organic compounds reagents and can be used as precursors for other classes of organic molecules in synthetic chemistry. Catalytic hydrogenolysis of C=OH bonds is a very important synthetic technique; it is widely used in organic synthesis [1-3], pharmaceutical production [4,5] and biomass conversion [6-8]. Reduction of alcohols to the corresponding hydrocarbon is usually accomplished sequence of steps. Conventionally, hydrogenolysis of C=OH bond is achieved with molecular hydrogen using noble metals as catalysts. In some cases, stoichiometric reducing agents such as metal hydrides are used. Nevertheless, these traditional hydrogenolysis methods have some drawbacks. One drawback is the use of molecular hydrogen or stoichiometric reducing agents that often causes safety and environmental problems, because molecular hydrogen and metal hydrides are flammable, explosive and hazardous. Another drawback is the use of high temperature and high-pressure that will necessitate expensive high-pressure equipment, thereby increasing the cost of the process and resulting in many troubles in manipulation. An additional drawback is its low selectivity due to the hash reaction conditions employed. In contrast to the traditional hydrogenolysis methods, catalytic transfer hydrogenolysis (CTH) uses hydrogen donors to provide hydrogen species in situ; hence it offers the possibility to overcome the drawbacks of the traditional hydrogenolysis methods.

CTH is an important synthetic technique in organic chemistry. As neither hydrogen containment nor a pressure vessel is required; the mild reaction conditions offer considerable advantages over the conventional method of catalytic hydrogenolysis. For the transfer hydrogenolysis or hydrogenation, it is necessary to select an efficient catalyst and suitable hydrogen donors. Recently, formic acid has been employed as the source of hydrogen and has many advantages in regards to handling, transport, and storage and can easily be generated form hydrogen gas and carbon dioxide.

Generally, metal (VIII group elements) such as palladium ruthenium and Raney nickel are employed as the catalysts for the transfer hydrogenolysis. Palladium is arguably one of the most powerful and versatile transition-metal catalysts which can be immobilized on various heterogeneous supports and be used for a variety of organic transformations. Palladium heterogeneous catalyst can be recycled by simple filtration and reused in several cycles without the loss of efficiency with the consequently advantages such as economic and environmental. Recently, we developed asymmetric carbocyclizations implementing a heterogeneous palladium catalyst with a simple chiral amine co-catalyst. However, it is not sure whether the Palladium heterogeneous catalyst could be reused for the CTH of alcohols.

OBJECT OF THE INVENTION

It is an objective of the invention to hydrocarbons from alcohols using a heterogeneous metal catalyst system.

Another objective of the invention is to synthesize hydrocarbons from aldehydes or ketones using a heterogeneous metal catalyst system.

Another objective of the invention is to depolymerize lignin followed by the above conversion of carbonyls or alcohols to hydrocarbons, respectively.

Another objective of the invention is to link it to selective catalytic oxidations of arylpolydiols such as lignin followed depolymerization and then conversion of carbonyls or alcohols to hydrocarbons, respectively.

A still further objective of the invention is to provide a method of the aforementioned kind that is advantageous from an environmental and health standpoint.

Even more objectives will become evident from a study of the summary of the invention, a number of preferred embodiments illustrated in a drawing, and the appended claims.

SUMMARY OF THE INVENTION

The invention is based on the use of a heterogeneous metal catalyst that can convert alcohols to hydrocarbons using a suitable reducing agent (Scheme 1).

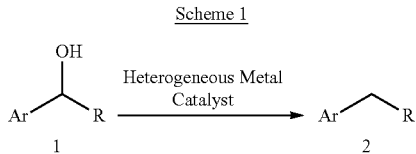

Another aspect of the invention is the use of a heterogeneous metal catalyst that can convert an ether bond beta to a hydroxyl group or alpha to a carbonyl group to hydrocarbons, respectively, using suitable reducing agents.

Another aspect of the invention is the use of a heterogeneous metal catalyst that can convert aldehydes or

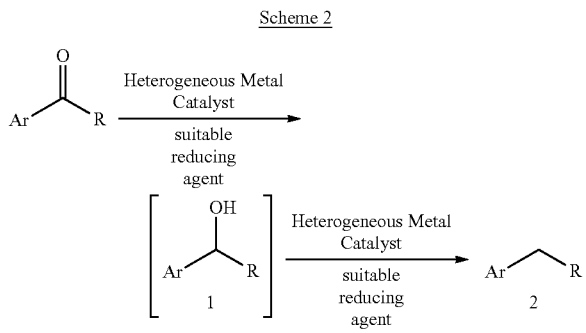

ketones to hydrocarbons, respectively, using suitable reducing agents (Scheme 2).

Another, aspect of the invention is the catalytic selective oxidation of primary or secondary alcohols of "lignin-type" structure to the corresponding carbonyl, respectively. Followed by one-pot depolymerization and then reduction by a heterogeneous metal catalyst to the corresponding hydrocarbon using a suitable reducing agent (Scheme 3).

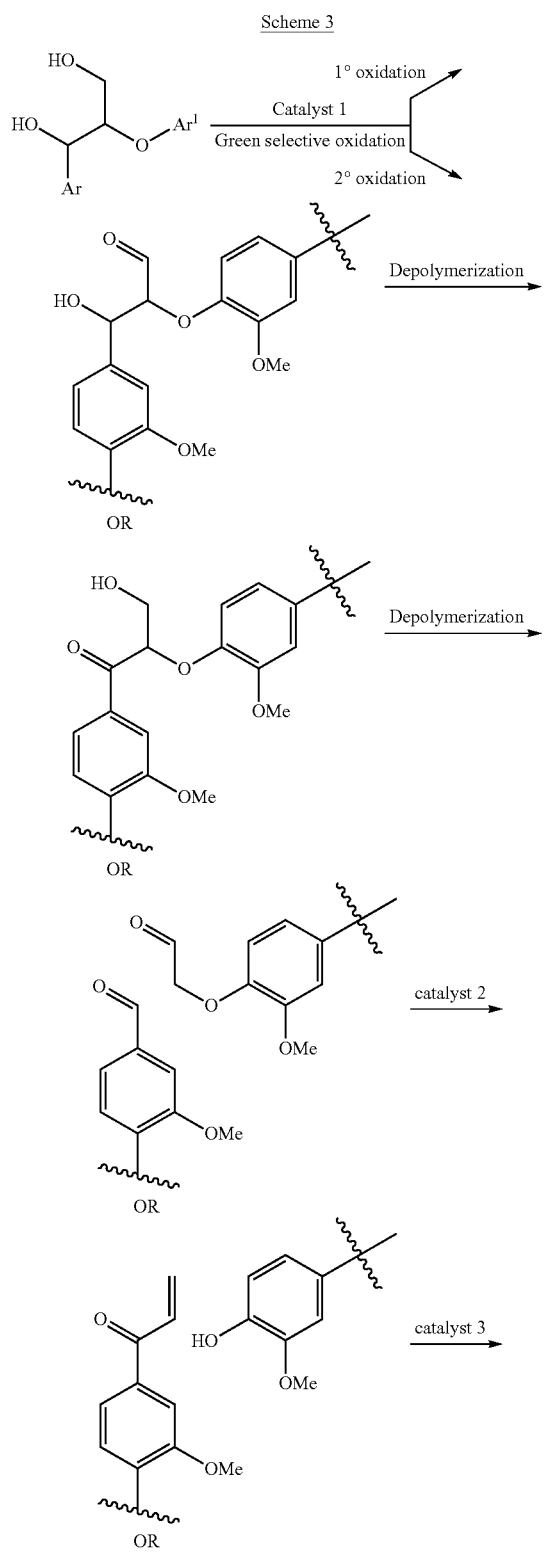

Scheme 3

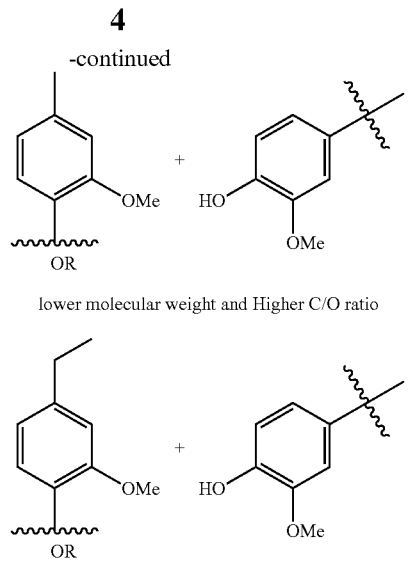

lower molecular weight and Higher C/O ratio

Another, aspect of the invention is the synthesis of hydrocarbons and similar compounds starting from lignin and its derivatives using a combination of selective oxidations followed by depolymerization.

The method of the invention is composed of key steps in which lignin is converted under environmentally benign conditions. In one embodiment of the invention the method comprises the steps of:
  i. Providing an alcohol
  ii. Chemically converting the said alcohol to a carbonyl by a suitable modification method, i.e. oxidation
  iii. Convert the carbonyl to another carbonyl compound using a suitable depolymerization system
  iv. Conversion of the carbonyl to the corresponding alcohol by using a suitable heterogeneous metal catalyst and reducing agent
  v. Conversion of the said alcohol to the corresponding hydrocarbon by using a suitable heterogeneous metal catalyst and reducing agent.

The oxidations can be performed in water or organic solvents. Suitable catalysts, depending on the nature of the reactive molecule, may be a heterogeneous metal catalyst, homogeneous metal catalyst, a metal-free catalyst, or an enzyme. Suitable oxidants, depending on the nature of the reactive molecule, may be oxygen, air, hydrogen peroxide.

The oxidized oligomer or polymer with a lignin-type structure is directly depolymerized to a smaller size carbonyl compound by using basic, oxidative, radical or organocatalytic conditions.

The carbonyl groups from the previous step are reduced to the corresponding alcohol by the heterogeneous catalyst using a suitable reducing agent. Suitable reducing agents, depending on the nature of the reactive molecule, may be hydrogen, formic acid, ammonium formiate.

The alcohol groups from the previous step are reduced to the corresponding hydrocarbons by the heterogeneous catalyst using a suitable reducing agent. Suitable reducing agents, depending on the nature of the reactive molecule, may be hydrogen, formic acid, ammonium formiate.

In another embodiment of the invention the method comprises the steps of:
  ii. Providing an aldehyde or ketone
  iii. Convert the carbonyl to another carbonyl compound using a suitable depolymerization system.

iv. Conversion of the carbonyl from step iii to the corresponding alcohol by using a suitable heterogeneous metal catalyst and reducing agent
v. Conversion of the said alcohol to the corresponding hydrocarbon by using a suitable heterogeneous metal catalyst and reducing agent.

The carbonyl groups are reduced to the corresponding alcohol by the heterogeneous catalyst using a suitable reducing agent. Suitable reducing agents, depending on the nature of the reactive molecule, may be hydrogen, formic acid, ammonium formiate.

The alcohol groups from the previous step are reduced to the corresponding alcohol by the heterogeneous catalyst using a suitable reducing agent. Suitable reducing agents, depending on the nature of the reactive molecule, may be hydrogen, formic acid, ammonium formiate.

Hence, in view of the above, the objects of the present is attained by a method of conversion of a C=O bond to a C—H bond, comprising the steps of:
i. Providing an alcohol and converting the alcohol to a compound comprising a C=O bond, wherein the compound comprising a C=O is selected from an aldehyde and a ketone, wherein the conversion of the alcohol to a compound comprising a C=O bond comprises the step of:
  a. Oxidation with an oxidant and catalyst, wherein the oxidant is selected from $H_2O_2$, $O_2$ and NaOCl, and wherein the catalyst is selected from heterogeneous supported metal catalyst, homogeneous organometallic complex, a metal-free catalyst (mediator), and enzyme (EC 1:10:3:2), and
ii. Providing the compound comprising a C=O bond from the previous step, and
iii. Reducing said compound comprising a C=O bond in a solvent comprising reducing agent and a catalyst, wherein the catalyst is selected from a heterogeneous metal catalyst and homogeneous organometallic complex, wherein the heterogeneous metal catalyst is a Pd(0)-nanocatalyst which is heterogeneously supported on silica containing material, wherein the homogeneous organometallic complex comprises Pd, Ir, Ru, Ni, Co, Cu complexes.

In a preferred embodiment of the present invention, the catalyst is a Pd-catalyst selected from Pd(0)-amino functionalized silica support, preferably Pd(0)-AmP-silica support.

In a further preferred embodiment, the catalyst is a Pd-catalyst selected from Pd(0)-AmP-MCF and Pd(0)-AmP-CPG, preferably the Pd-catalyst is recyclable.

In a further preferred embodiment, the reducing agents are ammonium formiate and $H_2$ gas, and wherein the solvent is preferably toluene. Moreover, the reduction may be carried out at a temperature of 20-80° C., preferably at ambient temperature or 80° C.

In a further preferred embodiment, the alcohol is converted to an aldehyde in step i), wherein the conversion of the alcohol to an aldehyde is conducted in the presence of NaOCl, TEMPO (2,2,6,6-Tetramethylpiperidin-1-yl)oxyl), NaOH, KBr and $O_2$, and wherein step i) may comprise the steps of:
a. Adding a solution of KBr to a solution comprising the alcohol and TEMPO, preferably KBR is in a water solution and TEMPO is in $CH_2Cl_2$,
b. Stirring the mixture, preferably at 0° C.,
c. NaOCl solution is added to the reaction mixture, preferably the NaOCl solution has pH 9,
d. Adding NaOH to the reaction mixture in the presence of $O_2$, and
e. Stirring the mixture, preferably at 0° C., more preferably at 0° for 3 hours.

In a further preferred embodiment, the alcohol is converted to a ketone in step i), wherein the conversion of the alcohol to a ketone is conducted in the presence of $O_2$, TEMPO, $HNO_3$ and HCl, and wherein step i) may comprise the steps of:
a. Adding TEMPO to the alcohol in the presence of $O_2$,
b. Adding a mixture of $HNO_3$ in acetonitrile,
c. Adding a mixture of HCl in acetonitrile, preferably also adding water and acetonitrile, and
d. Optionally heating the mixture.

In a further preferred embodiment, the alcohol is a diol, and wherein said diol is in step i) converted to an aldol which then undergoes a spontaneous catalytic retro-aldol reaction to the corresponding aldehyde moieties, and wherein the C=O bond of the aldehydes are subsequently reduced to a C—H bond in step iii).

In a further preferred embodiment, the diol is selected from lignin and derivatives thereof, preferably the alcohol is lignin containing benzylic, allylic or aliphatic alcohols including β-O-4 aryl ether linkages, more preferably the lignin is selected from milled wood lignin, cellulolytic lignin, organosolv lignin and technical lignin from pulping processes, wherein the method may comprise the steps of:
i. Providing lignin and oxidizing the lignin to a polymer comprising aldehyde groups,
ii. The polymer comprising aldehyde groups which have been provided in the previous step subsequently undergo spontaneous catalytic retro-aldol reaction which leads to a depolymerization,
iii. Reducing the aldehyde groups.

In a further preferred embodiment, the alcohol is a primary alcohol, and wherein the primary alcohol is converted to an aldehyde in step i), and wherein the C=O bond of the aldehyde is subsequently reduced to a C—H bond.

In a further preferred embodiment, the alcohol is selected from vanillyl alcohol, hydroxy-, methoxy- and ethoxybenzyl alcohols, and wherein vanillyl alcohol, hydroxy-, methoxy- and ethoxybenzyl alcohols are converted to their respective aldehydes in step i), and wherein the C=O bond of the aldehyde is subsequently reduced to a C—H bond.

In a further preferred embodiment, the alcohol is a secondary alcohol, and wherein said secondary alcohol is converted to a ketone in step i), and wherein the C=O bond of the ketone is subsequently reduced to a C—H bond.

In a further preferred embodiment, the object of the invention is attained by the products obtainable by the above preferred embodiments. Furthermore, the object of the invention is also attained by using said products as fuels.

The objects of the present is also attained by a method of conversion of a C—O or C=O bond to a C—H bond, comprising the steps of:
i. Providing a compound comprising a C—O bond or a C=O bond, wherein said compound is selected from an aldehyde, a ketone, an alcohol, an aldol, a compound having an ether bond beta to a hydroxyl group, or a compound having an ether bond alpha to a carbonyl group, and
ii. Reducing the C—O or C=O bond to a C—H bond in a solvent comprising reducing agent and a catalyst, wherein the catalyst is selected from heterogeneous metal catalyst and homogeneous organometallic complex, wherein the heterogeneous metal catalyst is a Pd(0)-nanocatalyst which is heterogeneously supported on silica containing material, wherein the homogeneous organometallic complex comprises Pd, Ir, Ru, Ni, Co, Cu complexes and wherein an optional step of providing an alcohol and then converting the alcohol to a compound comprising a C=O bond is provided before step i).

In a further embodiment, the catalyst is a Pd-catalyst selected from Pd(0)-amino functionalized silica support, preferably Pd(0)-AmP-silica support.

In a further preferred embodiment, the catalyst is a Pd-catalyst selected from Pd(0)-AmP-MCF and Pd(0)-AmP-CPG, preferably the Pd-catalyst is recyclable.

In a further preferred embodiment, the reducing agent is selected from hydrogen, formic acid and ammonium formiate.

In a further preferred embodiment, the reducing agent is ammonium formiate and formic acid when the compound comprising a C—O bond is an alcohol, and wherein the solvent may be ethanol and/or water, preferably a mixture of ethanol and water, more preferably the mixture of ethanol and water having a ratio of ethanol:water being 4:1. Moreover, ammonium formiate and formic acid may be added in a ratio of 0.25 and 6.6, respectively, in relation to the alcohol, or in a ratio of 0.25 and 3.3, respectively, in relation to the alcohol.

In a further preferred embodiment, the reducing agents are ammonium formiate and $H_2$ gas when the compound comprising a C=O bond is an aldehyde, ketone, an aldol, a compound having an ether bond beta to a hydroxyl group, or a compound having an ether bond alpha to a carbonyl group, and wherein the solvent is preferably toluene.

In a further preferred embodiment, the reduction is carried out at a temperature of 20-80° C., preferably at ambient temperature or 80° C., most preferably at ambient temperature.

In a further preferred embodiment, a step of providing an alcohol and then converting the alcohol to a compound comprising a C=O bond is provided before step i), wherein said alcohol is preferably selected from a diol, primary alcohol and secondary alcohol, most preferably said alcohol is lignin.

In a further preferred embodiment, the object of the invention is attained by the products obtainable by the above preferred embodiments. Furthermore, the object of the invention is also attained by using said products as fuels.

DETAILED DESCRIPTION

The present invention relates to a method of conversion of a C—O or C=O bond to a C—H bond. The method, comprises the steps of (i) providing a compound comprising a C—O bond or a C=O bond, and then (ii) reducing the C—O or C=O bond to a C—H bond. A compound comprising a C=O bond is for example an aldehyde molecule and the C=O bond is in the method according to the present invention reduced to a C—H bond, i.e. the aldehyde is reduced to its corresponding hydrocarbon.

The method of conversion of a C—O or C=O bond to a C—H bond can also be used in a method of converting lignin to fuels. However, the lignin must first undergo oxidization and depolymerization to compounds having aldehyde groups. The resulting C=O moieties of the aldehyde groups are thereafter reduced C—H moieties. The final product may be used as fuels.

It is important to note that the oxidization reaction is not limited only to lignin. Other alcohols, including primary alcohols, secondary alcohols and diols can all be subjected to the oxidization reaction which yields an aldehyde. Moreover, diols such as lignin can also be oxidized to ketones.

The oxidization reaction, i.e. conversion of an alcohol to a compound comprising a C=O bond (i.e. aldehyde or ketone), involves oxidation with an oxidant and catalyst. The oxidant may be selected from $H_2O_2$, $O_2$ and NaOCl, while the catalyst is selected from heterogeneous supported metal catalyst, homogeneous organometallic complex and a metal-free catalyst (mediator) and enzyme (EC 1:10:3:2). In the next step the compound comprising a C=O is reduced with a reducing agent and heterogeneous metal catalyst.

As already indicated, the alcohol (such as lignin) can be oxidized to an aldehyde or ketone. The conversion of the alcohol to an aldehyde is conducted in the presence of NaOCl, TEMPO (2,2,6,6-Tetramethylpiperidin-1-yl)oxyl), NaOH, KBr and $O_2$ (see Examples 9-12). First, a solution of KBr is added to a solution comprising the alcohol and TEMPO. The mixture is then stirred and a basic NaOCl solution is added to the reaction mixture followed by adding NaOH to the reaction mixture in the presence of $O_2$.

The alcohol is converted to a ketone in the presence of $O_2$, TEMPO, $HNO_3$ and HCl (see Example 8). The conversion involves adding TEMPO to the alcohol in the presence of $O_2$. In the next step $HNO_3$ and HCl are added to the mixture followed by heating.

When the alcohol is a diol, the diol is oxidized with oxidant and catalyst to an aldol which then undergoes a spontaneous catalytic retro-aldol reaction to the corresponding aldehyde moieties (see Examples 6 and 7). The C=O bonds of the aldehydes are subsequently reduced to a C—H bonds by the reducing agent and heterogeneous metal catalyst.

A preferred diol is lignin and derivatives thereof. The lignin may be selected from milled wood lignin, cellulosic lignin, organosolv lignin and technical lignin from pulping processes. The lignin is oxidized with oxidant and catalyst to a polymer comprising aldehyde groups which undergo spontaneous catalytic retro-aldol reaction which leads to a depolymerization (Example 13). In the subsequent step the aldehyde groups are reduced with reducing agent and heterogeneous metal catalyst. Moreover, the alcohol may be a primary alcohol which is first converted to an aldehyde and then the C=O group is reduced to a C—H bond. Primary alcohols may be selected from vanillyl alcohol, hydroxy-, methoxy- and ethoxybenzyl alcohols, and wherein vanillyl alcohol, hydroxy-, methoxy- and ethoxybenzyl alcohols.

A further alternative is to use a secondary alcohol which is first oxidized to a ketone wherein the C=O bond of the ketone is subsequently reduced to a C—H bond.

For the reduction step, the heterogeneous metal catalyst is a Pd(0)-nanocatalyst which is heterogeneously supported on silica containing material. The Pd-catalyst may selected from Pd(0)-amino functionalized silica support such as Pd(0)-AmP-silica support. Specific examples of Pd(0)-nanocatalyst are Pd(0)-AmP-MCF and Pd(0)-AmP-CPG (see Example 1). The Pd-catalyst is preferably recyclable (see Example 3 for recycling process). Alternatively, the catalyst may be a homogeneous organometallic complex which may have a complex comprising Pd, Ir, Ru, Ni, Co, Cu complexes (see Example 13).

The reducing agents for reducing the aldehyde or a ketone are ammonium formiate and $H_2$ gas. The reduction can be carried in various temperatures such as at 20-80° C. Although the reduction can be carried out at 80° C., ambient temperature (i.e. room temperature of about 22° C.) is more convenient than and as effective as higher temperatures (see Example 1).

Importantly, the products obtained by the above described methods (particularly the method involving lignin) can be used as fuels.

It should be noted that the method of converting a C—O or C=O bond to a C—H bond does not necessarily have to involve an oxidation reaction. Instead of having an alcohol such as lignin as a starting compound, the starting compound may be a compound having a C—O or C=O bond such as an aldehyde, a ketone, an alcohol, an aldol, a compound having an ether bond beta to a hydroxyl group, or a compound having an ether bond alpha to a carbonyl group. The C—O or C=O bond is reduced to a C—H bond by a reducing agent and heterogeneous metal catalyst (see Examples 1, 2, 4 and 5).

The heterogeneous metal catalyst is a Pd(0)-nanocatalyst which is heterogeneously supported on silica containing material, preferably recyclable. Specific examples of these types of catalyst have already been mentioned above (see also Example 1) and the reducing agent is selected from hydrogen, formic acid and ammonium formiate (See Examples 2, 4 and 5). Alternatively, the catalyst may be a homogeneous organometallic complex which may have a complex comprising Pd, Ir, Ru, Ni, Co, Cu complexes (see Example 13).

The reducing agent is ammonium formiate and formic acid when the compound comprising a C—O bond is an alcohol (Example 2). However, the reducing agents are ammonium formiate and $H_2$ gas when the compound comprising a C=O bond is an aldehyde (Example 5), ketone, an aldol, a compound having an ether bond beta to a hydroxyl group, or a compound having an ether bond alpha to a carbonyl group (Example 4).

The product obtainable by the above described reduction methods can be used as fuels.

EXAMPLES

General Methods (IR) spectra were recorded on Thermo Fisher Nicolet 6700 FT-IR spectrometer, $n_{max}$ in $cm^{-1}$. Bands are characterized as broad (br), strong (s), medium (m), or weak (w).

$^1H$ NMR spectra were recorded on a Bruker Avance (500 MHz) spectrometer. Chemical shifts are reported in ppm from tetramethylsilane with the solvent resonance resulting from incomplete deuterium incorporation as the internal standard (CDCl$_3$: δ 7.26 ppm). Data are reported as follows: chemical shift, multiplicity (s=singlet, d=doublet, q=quartet, br=broad, m=multiplet), and coupling constants (Hz), integration.

$^{13}C$ NMR spectra were recorded on a Bruker Avance (125.8 MHz or 100 MHz) spectrometer with complete proton decoupling. Chemical shifts are reported in ppm from tetramethylsilane with the solvent resonance as the internal standard (CDCl$_3$: δ 77.16 ppm).

High-resolution mass spectrometry was performed on Agilent 6520 Accurate-Mass Q-TOF LC/MS (positive mode).

Chemicals and solvents were either purchased puriss p. A. from commercial suppliers or were purified by standard techniques. Commercial reagents were used as purchased without any further purification.

Aluminum sheet silica gel plates (Fluka 60 F254) were used for thin-layer chromatography (TLC), and the compounds were visualized by irradiation with UV light (254 nm) or by treatment with a solution of phosphomolybdic acid (25 g), Ce(SO$_4$)$_2$.H$_2$O (10 g), conc. H$_2$SO$_4$ (60 mL), and H$_2$O (940 mL), followed by heating. Purification of the product was carried out by flash column chromatography using silica gel (Fluka 60, particle size 0.040-0.063 mm).

Example 1—Optimization Studies (Table 1)

A microwave-vial containing a solution of 1a (0.4 mmol, 1.0 equiv.), ammonium formiate and Pd(0)-Nanocatalyst (palladium-aminopropyl-mesocellular foam (Pd(0)-AmP-MCF), 26.8 mg, 0.02 mmol, 8 wt %, 5 mol %) [1] or (palladium-aminopropyl-controlled pore glass (Pd(0)-CPG), 569 Å, 148.0 mg, 0.02 mmol, 135 μmol/g) in EtOH (2.4 mL) and H$_2$O (0.6 mL) was stirred for 10 minutes at room temperature. Afterwards was added formic acid and the resulting mixture was stirred at room temperature for the time shown in table. NMR samples for NMR-yield were prepared by removing 0.05 mL aliquots from the reaction mixture, filtration through Celite using CDCl$_3$ (1.5 mL) as eluent and mesitylene was used as an internal standard.

TABLE 1

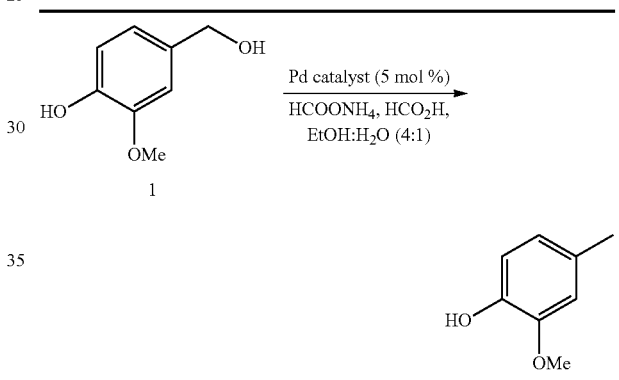

| Entry | Pd catalyst | HCOONH$_4$ (equiv.) | HCO$_2$H (equiv.) | temp (° C.) | time (h) | Conv. (%)$^a$ |
|---|---|---|---|---|---|---|
| 1 | Pd/C | 0.25 | 3.3 | 80 | 1 | 50[e] |
| 2 | Pd(0)-AmP-MCF | 0.25 | 3.3 | 80 | 0.5 | 78 |
| 3 | Pd(0)-AmP-MCF | 0.25 | 3.3 | 100 | 0.5 | 69 |
| 4 | Pd(0)-AmP-MCF | 0.50 | 3.3 | 80 | 0.5 | 74 |
| 5$^b$ | pd(0)-AmP-MCF | 0.25 | 3.3 | 80 | 0.5 | 49 |
| 6$^c$ | Pd(0)-AmP-MCF | 0.25 | 3.3 | 80 | 0.5 | 53 |
| 7 | Pd(0)-AmP-CPG | 0.25 | 3.3 | 80 | 0.5 | 54 |
| 8 | Pd(0)-AmP-MCF | 0.25 | — | 80 | 0.5 | <1 |
| 9 | Pd(0)-AmP-MCF | 3.0 | — | 80 | 0.5 | 45 |
| 10 | Pd(0)-AmP-MCF | 0.25 | 6.6 | 80 | 0.5 | 94 |
| 11 | Pd(0)-AmP-CPG | 0.25 | 6.6 | 80 | 0.5 | 51 |
| 12 | Pd(0)-AmP-MCF | 0.25 | 6.6 | 22 | 1 | >99 |
| 13 | Pd(0)-AmP-CPG | 0.25 | 6.6 | 22 | 1 | >99 |
| 14 | Pd/C | 0.25 | 6.6 | 22 | 1 | 41[e] |
| 15$^d$ | Pd(0)-AmP-MCF | 3.0 | — | 22 | 24 | 8 |
| 16$^d$ | Pd(0)-AmP-MCF | 3.0 | — | 80 | 9 | >99 |
| 17 | Pd(0)-AmP-MCF | — | 6.6 | 22 | 1 | 52 |
| 18 | Pd(0)-AmP-MCF | 0.25 | 6.0 | 22 | 1 |  |
| 19 | Pd(0)-AmP-MCF | 0.25 | 5.0 | 22 | 1 | >99 |

$^a$Determined by analysis of $^1$H-NMR of unpurified mixtures.
$^b$0 mol % MCF-Pd(0).
$^c$2.5 mol % MCF-Pd(0).
$^d$The reaction was performed with toluene.
$^e$The same conv after 24 h.

Example 2—Examples of Converting Alcohols to Hydrocarbon (Table 2)

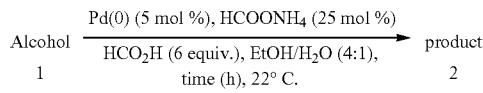

Procedure: A microwave-vial containing a solution of 1 (0.4 mmol, 1.0 equiv.), ammonium formiate (6.0 mg, 0.095 mmol, 25 mol %) and Pd(0)-Nanocatalyst (Pd(0)-AmP-MCF, 26.8 mg, 0.02 mmol, 8 wt %, 5 mol %) [2] or (Pd(0)-CPG, 569 Å, 148.0 mg, 0.02 mmol, 135 μmol/g) in EtOH (2.4 mL) and H$_2$O (0.6 mL) was stirred for 10 minutes at room temperature. Afterwards was added formic acid (0.09 mL, 2.4 mmol, 6 equiv.) and the resulting mixture was stirred at room temperature for the time shown in table. NMR samples for NMR-yield were prepared by removing 0.05 mL aliquots from the reaction mixture, filtration through Celite using CDCl$_3$ (1.5 mL) as eluent and mesitylene was used as an internal standard. Before the purification of the products, the crude reaction mixture was filtrated through Celite using CHCl$_3$ (10 mL) as eluent and evaporated. The crude material was purified by silica gel flash column chromatography.

TABLE 2

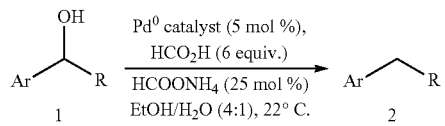

| Entry | Pd catalyst | Alcohol | Product | time (h) | Yield.(%)[a] |
|---|---|---|---|---|---|
| 1 | Pd(0)-AmP-MCF | (4-hydroxy-3-methoxybenzyl alcohol) | (2-methoxy-4-methylphenol) 2a | 1 | 95 |
| 2 | Pd(0)-AmP-CPG | | | 1 | 93[b] |
| 4 | Pd(0)-AmP-MCF | (4-nitrobenzyl alcohol) | (4-methylaniline) 2b | 1 | 93[b] |
| 5 | Pd(0)-AmP-MCF | (2,3-dimethoxybenzyl alcohol) | (1,2-dimethoxy-3-methylbenzene) 2c | 4 | 96 |
| 6 | Pd(0)-AmP-MCF | (benzyl alcohol) | (toluene) 2d | 1 | 94[b] |
| 7 | Pd(0)-AmP-CPG | | | 1 | 91[b] |
| 8 | Pd(0)-AmP-MCF | (1-phenylethanol) | (ethylbenzene) 2e | 1 | 96[b] |
| 9 | Pd(0)-AmP-MCF | (1-(4-aminophenyl)ethanol) | (4-ethylaniline) 2f | 1 | 93 |

TABLE 2-continued $$\text{Ar}\underset{1}{\overset{OH}{\underset{|}{C}}}\text{R} \xrightarrow[\text{HCOONH}_4 \text{ (25 mol \%)}]{\text{Pd}^0 \text{ catalyst (5 mol \%), HCO}_2\text{H (6 equiv.)}} \text{Ar}\underset{2}{\overset{}{\underset{|}{C}}}\text{R}$$
EtOH/H₂O (4:1), 22° C.

| Entry | Pd catalyst | Alcohol | Product | time (h) | Yield.(%)[a] |
|---|---|---|---|---|---|
| 10 | Pd(0)-AmP-MCF | 4-MeO-C₆H₄-CH(OH)-CH₃ (1g) | 4-MeO-C₆H₄-CH₂CH₃ (2g) | 8 | 98[b] |
| 11 | Pd(0)-AmP-MCF | Ph₂CH(OH) | Ph-CH₂-Ph (2h) | 1 | 97 |
| 12 | Pd(0)-AmP-MCF | Ph₃C(OH) | Ph₃CH (2i) | 1 | 92 |
| 13 | Pd(0)-AmP-MCF | Ph-CH(OH)-CH₂CH₃ (1j) | Ph-CH₂CH₂CH₃ (2j) | 3 | 91[b] |
| 14 | Pd(0)-AmP-CPG | Ph-CH(OH)-CH₂CH₃ (1j) | Ph-CH₂CH₂CH₃ (2j) | 3 | 90[b] |

[a] Isolated yield of pure 2.
[b] H-NMR yield using mesitylene as internal standard.

Characterization of Products

Toluene

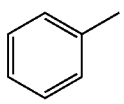

Spectra identical to the reported [3]; ¹H NMR (500 MHz, CDCl₃): δ 7.20-7.15 (m, 2H), 7.11-7.05 (m, 3H), 2.28 (s, 3H).

p-Toluidine

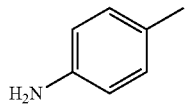

Spectra identical to the reported [4]; ¹H NMR (500 MHz, CDCl₃): δ 6.93 (d, J=8.7 Hz, 2H), 6.62 (d, J=8.6 Hz, 2H), 2.18 (s, 3H).

1,2-dimethoxy-3-methylbenzene

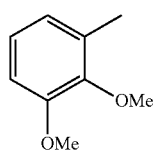

Colorless oil; IR (neat) n 2935 (m), 2834 (w), 1586 (m), 1484 (s), 1425 (m), 1268 (s), 1222 (s), 1174 (m), 1081 (s), 1009 (s), 805 (w), 747 (s), 686 (m); ¹H NMR (500 MHz, CDCl₃): δ 6.95 (t, J=8.2 Hz, 1H), 6.78-6.75 (m, 2H), 3.85 (s, 3H), 3.80 (s, 3H), 2.28 (s, 3H); ¹³C NMR (125.8 MHz, CDCl₃): δ 152.9, 147.5, 132.2, 123.8, 123.0, 110.1, 60.2, 55.8, 15.9; HRMS (ESI⁺) [M+H]⁺ calcd for C₉H₁₃O₂: 153.0916. found: 153.0906.

2-methoxy-4-methylphenol

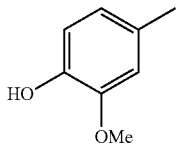

Colorless oil; IR (neat) n 3511 (b), 2923 (m), 1608 (w), 1514 (s), 1464 (m), 1364 (w), 1271 (s), 1234 (m), 1206 (m), 1150 (m), 1122 (w), 1034 (m), 919 (w), 810 (m), 590 (w), 559 (w) cm$^{-1}$; $^1$H NMR (500 MHz, CDCl$_3$): d 6.83 (d, J=7.9 Hz, 1H), 6.71-6.67 (m, 2H), 5.45 (s, 1H), 3.89 (s, 3H), 2.31 (s, 3H); $^{13}$C NMR (125.8 MHz, CDCl$_3$): δ 146.2, 143.3, 129.6, 121.5, 114.1, 111.6, 55.8, 21.0; HRMS (ESI$^+$) [M+H]$^+$ calcd for C$_8$H$_{11}$O$_2$: 139.0759. found: 139.0752.

1-ethylbenzene

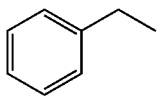

Spectra identical to the reported [5]; $^1$H NMR (500 MHz, CDCl$_3$): δ 7.28 (m, 2H). 7.18 (m, 3H), 2.65 (q, 2H, J=7.5 Hz), 1.24 (t, 3H, J=7.5 Hz).

4-ethylbenzenamine

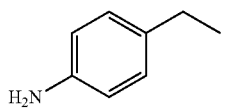

Brown solid; IR (neat) n 3354 (b), 2963 (m), 2929 (m), 2870 (m), 2360 (w), 1686 (s), 1612 (m), 1516 (s), 1455 (w), 1411 (m), 1310 (m), 1180 (w), 1123 (w), 827 (m), 755 (m), 474 (w) cm$^{-1}$; $^1$H NMR (500 MHz, CDCl$_3$): δ 7.03 (d, J=8.4 Hz, 2H), 6.69 (d, J=8.4 Hz, 2H), 5.79 (s, 2H), 2.57 (m, 2H), 1.21 (t, J=7.6 Hz, 3H); $^{13}$C NMR (125.8 MHz, CDCl$_3$): δ 128.3, 128.3, 128.2, 120.3, 119.3, 118.0, 28.0, 15.5; HRMS (ESI$^+$) [M+H]$^+$ calcd for C$_8$H$_{12}$N 122.0969. found: 122.0965.

1-ethyl-4-methoxybenzene

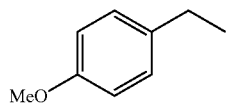

Spectra identical to the reported [6]; $^1$H NMR (500 MHz, CDCl$_3$): 7.11 (d, J=8.5 Hz, 2H), 6.83 (d, J=8.5 Hz, 2H), 3.78 (s, 3H), 2.59 (q, J=7.6 Hz, 2H), 1.21 (t, J=7.6 Hz, 3H).

Diphenylmethane

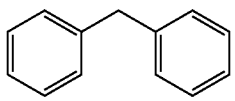 [SMILES: c1ccc(Cc2ccccc2)cc1]

White solid; IR (neat) n 3060 (w), 3025 (w), 2907 (w), 2842 (w), 1598 (w), 1492 (m), 1450 (m), 1075 (w), 1028 (w), 729 (s), 715 (s), 606 (m), 551 (w), 456 (m) cm$^{-1}$; $^1$H NMR (500 MHz, CDCl$_3$): δ 7.34-7.27 (m, 4H), 7.24-7.18 (m, 6H), 4.00 (s, 2H); $^{13}$C NMR (125.8 MHz, CDCl$_3$): δ 141.3, 129.1 (4C), 128.6 (4C), 126.2 (3C), 42.1; HRMS (ESI$^+$) [M–H]$^+$ calcd for C$_{13}$H$_{11}$ 167.0861. found: 167.0854.

Triphenylmethane

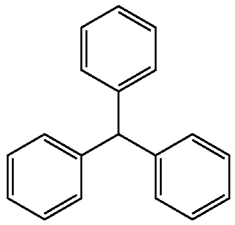 [SMILES: c1ccc(C(c2ccccc2)c2ccccc2)cc1]

White solid; IR (neat) n 3462 (b), 3060 (w), 1596 (w), 1489 (m), 1443 (m), 1326 (w), 1154 (m), 1068 (w), 1007 (m), 889 (m), 755 (s), 694 (s), 636 (s), 581 (m), 466 (m) cm$^{-1}$; $^1$H NMR (500 MHz, CDCl$_3$): δ 7.36-7.30 (m, 15H), 2.82 (s, 1H); $^{13}$C NMR (125.8 MHz, CDCl$_3$): δ 146.8, 128.6-127.23 (m), 82.0; HRMS (ESI$^+$) [M–H]$^+$ calcd for C$_{19}$H$_{15}$ 243.1174. found: 243.1168.

1-propylbenzene

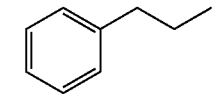

Spectra identical to the reported [7]. $^1$H NMR (500 MHz, CDCl$_3$)[7]: 7.42-7.04 (m, 5H), 2.49 (t, 2H), 2.05-1.82 (m, 2H), 0.9 (t, 3H).

Example 3—Procedure for the Recycling of the Pd Nanoparticles (Table 3)

A microwave-vial containing a solution of 1a (61.7 mg, 0.4 mmol, 1.0 equiv.), ammonium formate (6.0 mg, 0.095 mmol, 25 mol %) and Pd(0)-Nanocatalyst (Pd(0)-AmP-MCF, 26.8 mg, 0.02 mmol, 8 wt %, 5 mol %) [8] or (Pd(0)-CPG, 569 Å, 148.0 mg, 0.02 mmol, 135 μmol/g) in EtOH (2.4 mL) and H$_2$O (0.6 mL) was stirred for 10 minutes at room temperature. Afterwards was added formic acid (121.6 mg, 0.1 mL, 2.64 mmol, 6.6 equiv.) and the resulting mixture was stirred at room temperature for 1 h. Next, the reaction mixture was transferred to a centrifuge-vial and EtOH (8 mL) was added and after centrifugation, the supernatant liquid was removed and the catalyst washed with EtOH (8 mL) 3 times. Afterwards the catalyst was dried under vacuum and then washed with $CH_2Cl_2$ (8 mL) three times and then dried under vacuum.

TABLE 3

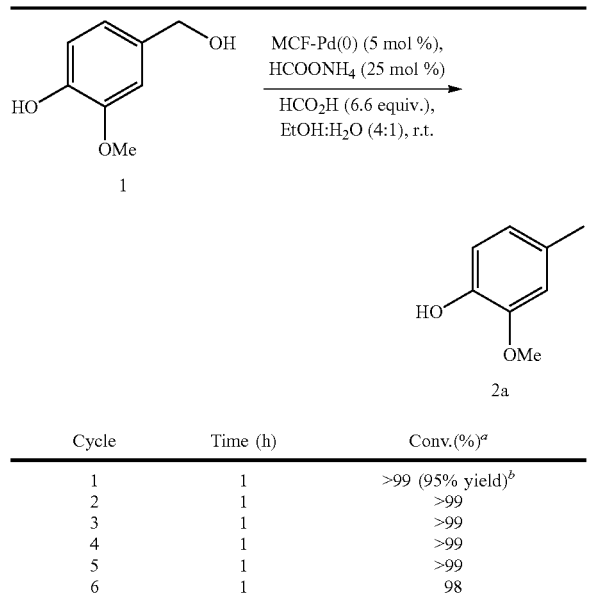

| Cycle | Time (h) | Conv.(%)[a] |
|---|---|---|
| 1 | 1 | >99 (95% yield)[b] |
| 2 | 1 | >99 |
| 3 | 1 | >99 |
| 4 | 1 | >99 |
| 5 | 1 | >99 |
| 6 | 1 | 98 |

[a]Determined by analysis of $^1$H-NMR of unpurified mixtures.
[b]pure isolated 2a

Example 4—Example of Ether Cleavage

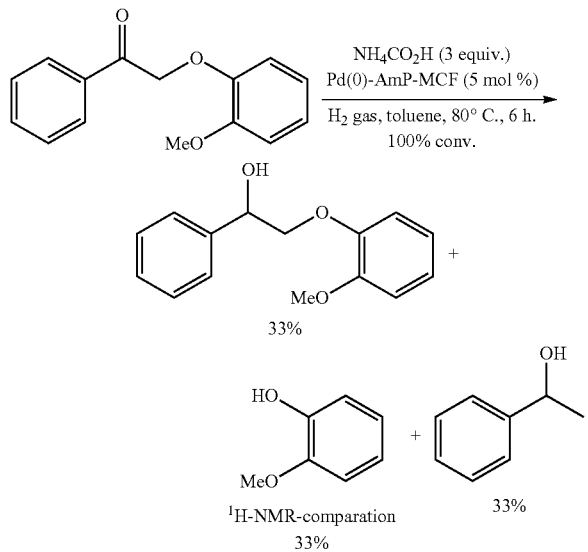

Example 5—Example of Deoxygenation of Aldehydes

A microwave-vial containing a solution of aldehyde (0.1 mmol, 1.0 equiv.), ammonium formiate (18.9 mg, 0.3 mmol, 3.0 equiv.) and Pd(0)-Nanocatalyst (Pd(0)-AmP-MCF, 6.7 mg, 0.005 mmol, 8 wt %, 5 mol %) in toluene (0.5 mL) under $H_2$ conditions was stirred at 80° C. for 6 h.

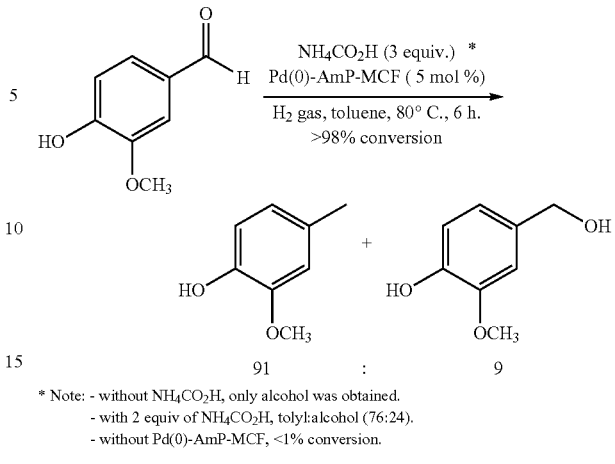

\* Note: - without $NH_4CO_2H$, only alcohol was obtained.
 - with 2 equiv of $NH_4CO_2H$, tolyl:alcohol (76:24).
 - without Pd(0)-AmP-MCF, <1% conversion.

Example 6—General Procedure for Selective Oxidation/Depolymerization Sequence

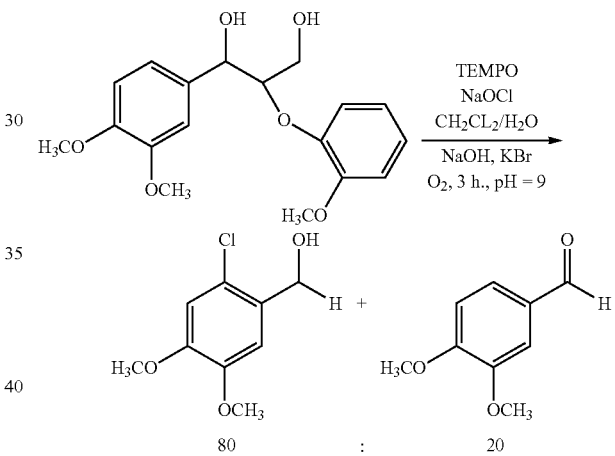

A solution of KBr (1.2 mg, 0.01 mmol, 10 mol %) in water (1 mL) were added to a solution containing lignin model (0.1 mmol, 1.0 equiv.) and TEMPO (1.6 mg, 0.01 mmol, 10 mol %) in $CH_2Cl_2$ (4 mL) and stirred at 0° C. Then, NaOCl (5.3 g, 10 mmol, 100 equiv.) solution with pH 9 was added drop wise to the reaction mixture. Afterwards, was added NaOH (2M, 3 mL) to the reaction mixture and connected balloon with $O_2$ and stirred at 0° C. for 3 h. After this time, the aqueous layer was extracted two times with $CH_2CL_2$ and the combined organic layers were washed with $H_2O$ two times, dried over anhydrous $Na_2SO_4$ and concentrated under reduced pressure. The crude material was purified by silica gel flash column chromatography obtaining the major product (Cl product): $^1$H NMR (500 MHz, $CDCl_3$): δ 10.32 (s, 1H), 7.41 (s, 1H), 6.90 (s, 1H), 3.97 (s, 3H), 3.92 (s, 3H). $^{13}$C NMR (125.8 MHz, $CDCl_3$): δ 188.7, 154.5, 148.4, 132.0, 125.4, 112.4, 109.77, 56.5, 56.2.

Example 7—Procedure for Selective Oxidation/Depolymerization/Deoxygenation Sequence A solution of KBr (1.2 mg, 0.01 mmol, 10 mol %) in water (1 mL) were added to a solution containing "diol lignin model" (0.1 mmol, 1.0 equiv.) and TEMPO (1.6 mg, 0.01 mmol, 10 mol %) in CH₂Cl₂ (4 mL) and stirred at 0° C. Then, NaOCl (5.3 g, 10 mmol, 100 equiv.) solution with pH 9 was added drop wise to the reaction mixture. Afterwards, was added NaOH (2M, 3 mL) to the reaction mixture and connected balloon with O₂ and stirred at 0° C. for 3 h. After this time, the aqueous layer was extracted two times with CH₂Cl₂. The solvent was removed. Ammonium formiate (18.9 mg, 0.3 mmol, 3.0 equiv.) and Pd(0)-Nanocatalyst (Pd(0)-AmP-MCF, 6.7 mg, 0.005 mmol, 8 wt %, 5 mol %) and toluene (0.5 mL) were added. The reaction was stirred at 80° C. for 6 h under H₂ atmosphere.

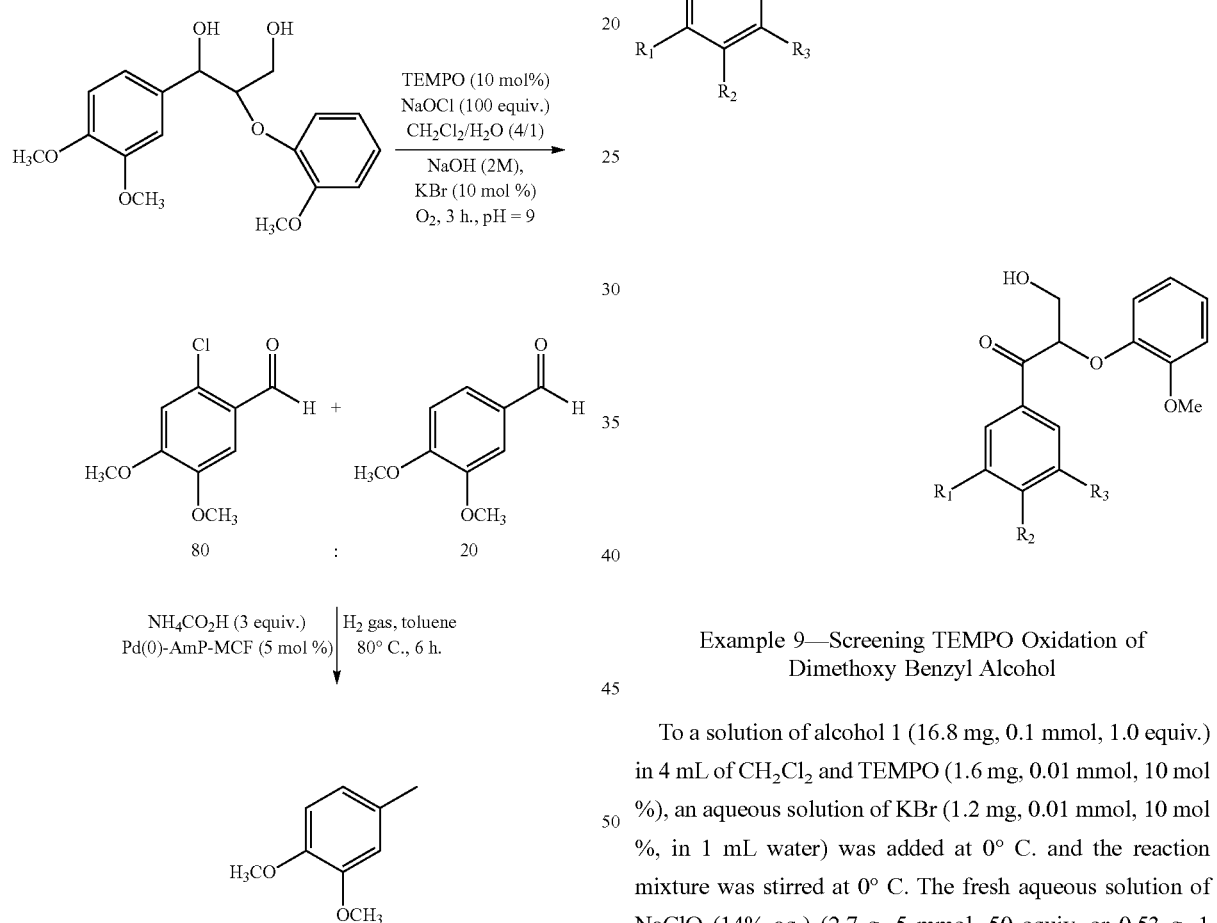

Example 8—General Procedure for the TEMPO Oxidation to Ketone

A microwave vial was loaded with diol 3 (33.4 mg, 0.1 mmol, 1.0 equiv.) and TEMPO (0.8 mg, 0.005 mmol, 5 mol %) and flushed with oxygen using O₂-balloon for 5 minutes, followed by addition of 100 μL of a solution from a mixture of 10 μL of HNO₃ in 1 mL acetonitrile and then 100 μL of a solution from a mixture of 10 μL HCl in 1 mL acetonitrile. Afterwards acetonitrile (300 μL) and water (30 μL) was added and then the vial was sealed and heated to 45° C. for 20 h. Subsequently, the organic phase was separated and water phase was washed with CH₂Cl₂. The collected organic phases were dried over Na₂SO₄, and concentrated by reduced pressure. The crude material was further purified by silica chromatography giving pure products 8 in 99% yield.

Example 9—Screening TEMPO Oxidation of Dimethoxy Benzyl Alcohol

To a solution of alcohol 1 (16.8 mg, 0.1 mmol, 1.0 equiv.) in 4 mL of CH₂Cl₂ and TEMPO (1.6 mg, 0.01 mmol, 10 mol %), an aqueous solution of KBr (1.2 mg, 0.01 mmol, 10 mol %, in 1 mL water) was added at 0° C. and the reaction mixture was stirred at 0° C. The fresh aqueous solution of NaClO (14% aq.) (2.7 g, 5 mmol, 50 equiv. or 0.53 g, 1 mmol, 10 equiv.) by adjusting pH at 9 with saturated NaHCO₃. Afterwards 2 M NaOH (3 mL) was added slowly. The reaction mixture was stirred for 1 h or 24 h in presence of O₂ gas at 0° C. Afterwards the organic phase was separated and water phase was washed with CH₂Cl₂. The collected organic phases were dried over Na₂SO₄, and concentrated by reduced pressure. The crude material was further purified by silica chromatography giving pure products 5.

| entry | NaOCl (equiv.) | time | yield[b] | Ratio (5a:5b:5c)[c] |
|---|---|---|---|---|
| 1[d,e] | 10 | 24 | n.d | 86:4:10 (52:37:11)[f] |
| 2[d,e] | 50 | 1 | 83 | 48:52:0 |
| 3[d,e] | 50 | 1 | 87 | 19:75:6 |
| 4 | 10 | 24 | n.d. | 86:4:10 |
| 5[e] | 50 | 1 | 85 | 54:30:16 (35:65:0)[f] |

[a] According to ¹H NMR the conversion of all reactions were 100%.

[b]Yield of purified product 5 after silica chromatography.

[c]Determined by ¹H NMR analysis of crude reaction mixture

[d]The reaction was run without O₂ balloon.

[e]The reaction mixture was neutralizied to pH 7 before workup.

[f]The ratios of the products changed after work up.

Example 10—Screening TEMPO Oxidation of Lignin Model

To a solution of diol 3 (33.4 mg, 0.1 mmol, 1.0 equiv.) in 4 mL of CH$_2$Cl$_2$ and TEMPO (1.6 mg, 0.01 mmol, 10 mol %), an aqueous solution of KBr (1.2 mg, 0.01 mmol, 10 mol %, in 1 mL water) was added at 0° C. and the reaction mixture was stirred at 0° C. The fresh aqueous solution of NaClO (14% aq.) (2.7 g, 5 mmol, 50 equiv. or 0.53 g, 1 mmol, 10 equiv.) by adjusting pH at 9 with saturated NaHCO$_3$. Afterwards 2 M NaOH (3 mL) was added slowly. The reaction mixture was stirred for 1 h or 24 h in presence of O$_2$ gas at 0° C. Afterwards the organic phase was separated and water phase was washed with CH$_2$Cl$_2$. The collected organic phases were dried over Na$_2$SO$_4$, and concentrated by reduced pressure. The crude material was further purified by silica chromatography giving pure products 5 and 8.

| entry | NaOCl (equiv.) | time | yield[b] | Ratio (5a:5b:8)[c] |
|---|---|---|---|---|
| 1[d,e] | 10 | 24 | n.d | 100:0:0 |
| 2[d,f] | 50 | 1 | 52 | 21:70:9 |
| 3[d] | 50 | 1 | 50 | 37:38:25 |
| 4 | 50 | 1 | 51 | 29:51:20 |

[a] According to ¹H NMR the conversion of all reactions were 100%.

[b]Yield of purified product 5 and 8 after silica chromatography.

[c]Determined by ¹H NMR analysis of crude reaction mixture

[d]The reaction was run without O₂ balloon.

[e]the conversion of reaction was 20%.

[f]The reaction mixture was neutralized by pH 7 before workup.

Example 11—Screening TEMPO Oxidation of Two Substituted Lignin Models

To a solution of alcohol 1 or diol 3 (0.1 mmol, 1.0 equiv.) in 4 mL of CH$_2$Cl$_2$ and TEMPO (1.6 mg, 0.01 mmol, 10 mol %), an aqueous solution of KBr (1.2 mg, 0.01 mmol, 10 mol %, in 1 mL water) was added at 0° C. and the reaction mixture was stirred at 0° C. The fresh aqueous solution of NaClO (14% aq.) (2.7 g, 5 mmol, 50 equiv.) by adjusting pH at 9 with saturated NaHCO$_3$. Afterwards 2 M NaOH (3 mL) was added slowly. The reaction mixture was stirred for 1 h in presence of O$_2$ gas at 0° C. Afterwards the organic phase was separated and water phase was washed with CH$_2$Cl$_2$. The collected organic phases were dried over Na$_2$SO$_4$, and concentrated by reduced pressure. The crude material was further purified by silica chromatography giving pure products 4.

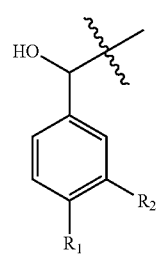
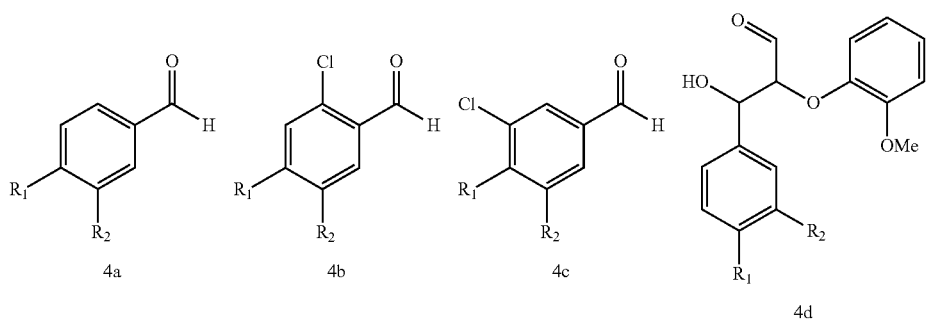
| entry | substrate | NaOCl (equiv.) | time | yield[b] | Ratio (4a:4b:4c:4d)[c] |
|---|---|---|---|---|---|
| 1 | 1a | 50 | 1 | 85 | 54:30:16 |
| 2 | 1b | 50 | 1 | 70 | 38:54:8 |
| 3 | 3a | 50 | 1 | 51 | 29:51:0:20 |

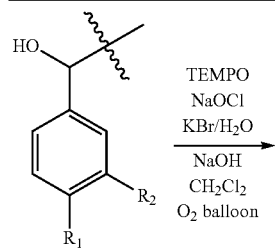

1 or 3
R₁, R₂ = OMe, OBn

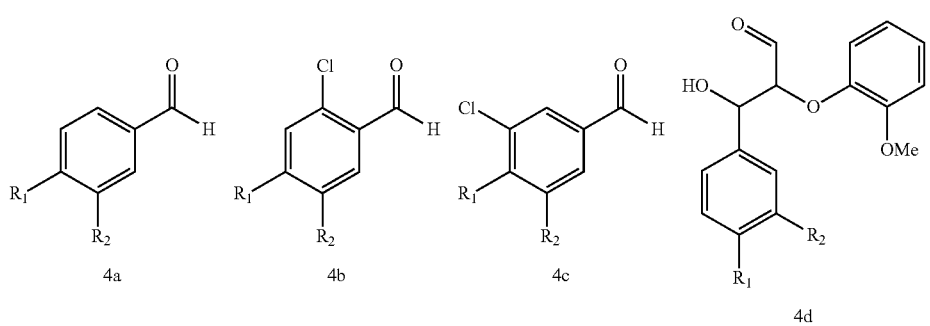

| entry | substrate | NaOCl (equiv.) | time | yield[b] | Ratio (4a:4b:4c:4d)[c] |
|---|---|---|---|---|---|
| 4 | 3b | 50 | 1 | 50 | 60:40:0:0 |

[a] According to ¹H NMR the conversion of all reactions were 100%.
[b] Yield of purified product 4 after silica chromatography.
[c] Determined by ¹H NMR analysis of crude reaction mixture

Example 12—TEMPO Oxidation of Three Substituted Lignin Models

To a solution of alcohol 1 or diol 3 (0.1 mmol, 1.0 equiv.) in 4 mL of $CH_2Cl_2$ and TEMPO (1.6 mg, 0.01 mmol, 10 mol %), an aqueous solution of KBr (1.2 mg, 0.01 mmol, 10 mol %, in 1 mL water) was added at 0° C. and the reaction mixture was stirred at 0° C. The fresh aqueous solution of NaClO (14% aq.) (2.7 g, 5 mmol, 50 equiv.) by adjusting pH at 9 with saturated $NaHCO_3$. Afterwards 2 M NaOH (3 mL) was added slowly. The reaction mixture was stirred for 1 h in presence of $O_2$ gas at 0° C. Afterwards the organic phase was separated and water phase was washed with $CH_2Cl_2$. The collected organic phases were dried over $Na_2SO_4$, and concentrated by reduced pressure. The crude material was further purified by silica chromatography giving pure products 7.

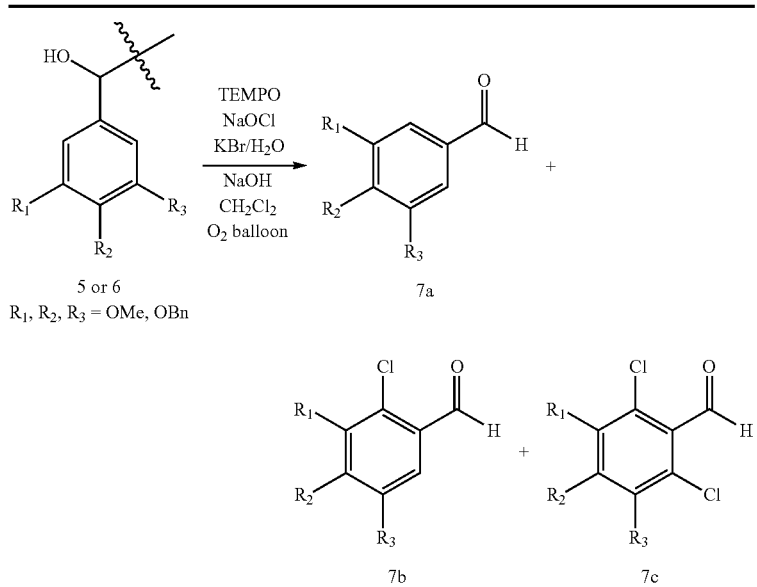
| entry | substrate | NaOCl (equiv.) | time | yield[b] | Ratio (7a:7b:7c)[c] |
|---|---|---|---|---|---|
| 1 | 5a (MeO, MeO, OMe, CH2OH) | 50 | 1 | 74 | 8:80:12 |
| 2 | 5b (MeO, BnO, OMe, CH2OH) | 50 | 1 | 75 | 0:51:49 |
| 3 | 6a | 50 | 1 | 53 | 0:80:20 |

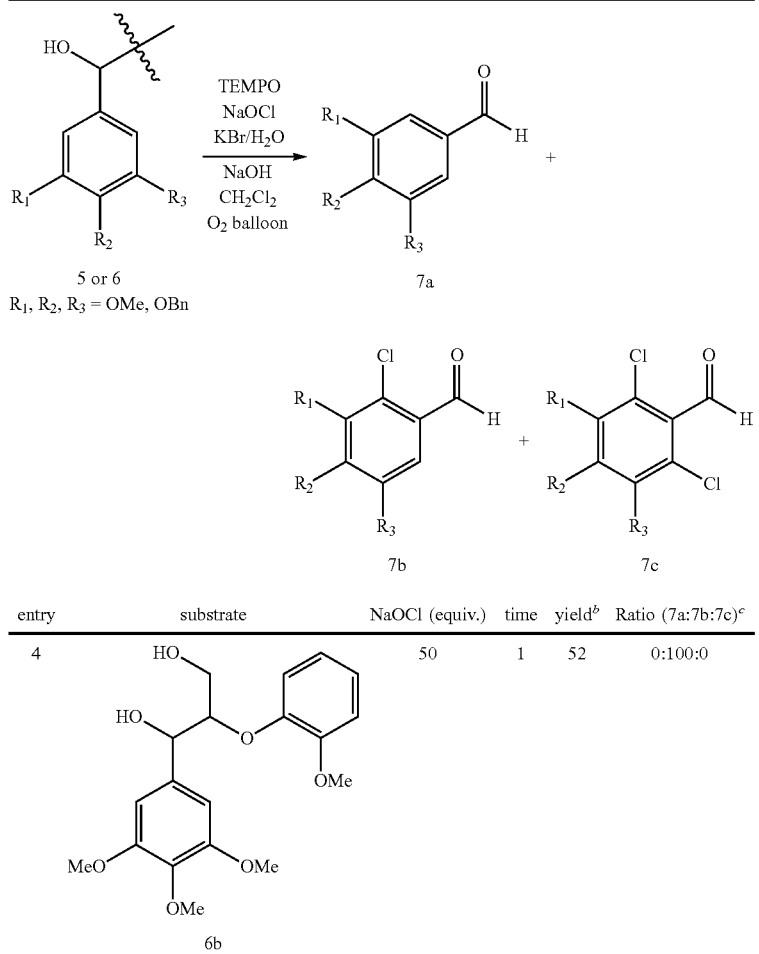

[a] According to ¹H NMR the conversion of all reactions were 100%.
[b] Yield of purified product 7 after silica chromatography.
[c] Determined by ¹H NMR analysis of crude reaction mixture Example 13—Procedure for Selective Oxidation/Depolymerization/Deoxygenation Sequence of Lignins (Containing Benzylic, Allylic or Aliphatic Alcohols Including β-O-4 Aryl Ether Linkages)

A solution of KBr (1.2 mg, 0.01 mmol, 10 mol %) in water (1 mL) were added to a solution containing lignin (0.1 mmol, 1.0 equiv.) and TEMPO (1.6 mg, 0.01 mmol, 10 mol %) in $CH_2Cl_2$ (4 mL) and stirred at 0° C. Then, NaOCl (5.3 g, 10 mmol, 100 equiv.) solution with pH 9 was added drop a drop to the reaction mixture. Afterwards, was added NaOH (2M, 3 mL) to the reaction mixture and connected balloon with $O_2$ and stirred at 0° C. for 3 h. After this time, the aqueous layer was extracted two times with $CH_2Cl_2$. The solvent was removed. Ammonium formate (18.9 mg, 0.3 mmol, 3.0 equiv.) and Pd(0)-Nanocatalyst (Pd(0)-AmP-MCF, 6.7 mg, 0.005 mmol, 8 wt %, 5 mol %) and toluene (0.5 mL) were added. The reaction was stirred at 80° C. for 6 h under $H_2$ atmosphere.

Lignin (containing benzylic, allylic or aliphatic alcohols including β-O-4 aryl ether linkages) was employed as substrates. The lignin can be milled wood lignin (MWL), cellulolytic enzyme lignin (CEL), organosolv lignin or a technical lignin from the pulping processes.

The selective oxidation/depolymerization/deoxygenation sequence of lignins can be employed using different transition metal (e.g. Pd, Ir, Ru, Ni, Co, Cu) complexes.

REFERENCES

References for Background of Invention

[1] V. S. Ranade, R. Prins, Chem. Eur. J. 2000, 6, 313.
[2] M. Yasuda, Y. Onishi, M. Ueba, T. Miyai, A. Baba, J. Org. Chem. 2001, 66, 7741.
[3] J. Muzart, Tetrahedron 2005, 61, 9423.
[4] C. Haiyan, L. Yongcheng, C. Guangying, H. Guping, W. Li, V. L. Chemistry of Natural Compounds 2006, 42, 407.
[5] N. Thakar, N. F. Polder, K. Djanashvili, H. van Bekkum, F. Kapteijn, J. A. Moulijn, J. Catal. 2007, 246, 344.
[6] M. Schlaf, J. Chem. Soc., Dalton Trans. 2006, 4645.
[7] J. Feng, J.-B. Wang, Y.-F. Zhou, H.-Y. Fu, H. Chen, X.-J. Li, Chem. Lett. 2007, 36, 1274.
[8] J. Feng, M.-L. Yuan, H. Chen, X.-J. Li, Prog. Chem. 2007, 19, 651.

References for the Example Section of the Detailed Description 1. a) E. W. Ping, R. Wallace, J. Pierson, T. F. Fuller and C. W. Jones, Micropor. Mesopor. Mater., 2010, 132, 174-180
   b) M. Shakeri, C. Tai, E. Göthelid, S. Oscarsson and J. Bäckvall, Chem. Eur. J., 2011, 17, 13269-13273
   c) E. V. Johnston, O. Verho, M. D. Kärkäs, M. Shakeri, C. Tai, P. Palmgren, K. Eriksson, S. Oscarsson and J. Bäckvall, Chem. Eur. J., 2012, 18, 12202-12206
   d) L. Deiana, S. Afewerki, C. Palo-Nieto, O. Verho, E. V. Johnston and A. Cordova, Sci. Rep., 2012, 2, 851; DOI: 10.1038/srep00851
2. a) E. W. Ping, R. Wallace, J. Pierson, T. F. Fuller and C. W. Jones, Micropor. Mesopor. Mater., 2010, 132, 174-180
   b) M. Shakeri, C. Tai, E. Göthelid, S. Oscarsson and J. Bäckvall, Chem. Eur. J., 2011, 17, 13269-13273
   c) E. V. Johnston, O. Verho, M. D. Kärkäs, M. Shakeri, C. Tai, P. Palmgren, K. Eriksson, S. Oscarsson and J. Bäckvall, Chem. Eur. J., 2012, 18, 12202-12206
   d) L. Deiana, S. Afewerki, C. Palo-Nieto, O. Verho, E. V. Johnston and A. Córdova, Sci. Rep., 2012, 2, 851; DOI: 10.1038/srep00851
3. Buser et al., Chemical Communications, 2014, 50 (32), 4234.
4. Berger et al., Magnetic Resonance in Chemistry, 2013, 51(12), 815.
5. Lancaster et al., Photochemistry and Photobiology, 2014, 90(2), 394.
6. Nyquist et al., Applied Spectroscopy, 1991, 45, 1649
7. Eisch et al., Organometallics, 2005, 24, 3355.
8. a) E. W. Ping, R. Wallace, J. Pierson, T. F. Fuller and C. W. Jones, Micropor. Mesopor. Mater., 2010, 132, 174-180
   b) M. Shakeri, C. Tai, E. Göthelid, S. Oscarsson and J. Bäckvall, Chem. Eur. J., 2011, 17, 13269-13273
   c) E. V. Johnston, O. Verho, M. D. Kärkäs, M. Shakeri, C. Tai, P. Palmgren, K. Eriksson, S. Oscarsson and J. Bäckvall, Chem. Eur. J., 2012, 18, 12202-12206
   d) L. Deiana, S. Afewerki, C. Palo-Nieto, O. Verho, E. V. Johnston and A. Córdova, Sci. Rep., 2012, 2, 851; DOI: 10.1038/srep00851

The invention claimed is:

1. A method of conversion of a C=O bond to a C—H bond, comprising the steps of:
   i. providing an alcohol and converting the alcohol to a compound comprising a C=O bond, wherein the compound comprising a C=O is selected from the group consisting of an aldehyde and a ketone, wherein the conversion of the alcohol to a compound comprising a C=O bond comprises the step of:
      oxidation with an oxidant and catalyst, wherein the oxidant is selected from the group consisting of $H_2O_2$, $O_2$, and NaOCl, and wherein the catalyst is selected from the group consisting of heterogeneous supported metal catalyst, homogeneous organometallic complex, metal-free catalyst (mediator), and enzyme (EC 1:10:3:2);
   ii. providing the compound comprising a C=O bond from the previous step; and
   iii. reducing said compound comprising a C=O bond in a solvent comprising reducing agent and a catalyst, wherein the catalyst is selected from the group consisting of a heterogeneous metal catalyst and homogeneous organometallic complex, wherein the catalyst is a Pd-catalyst selected from the group consisting of Pd(0)-AmP-MCF and Pd(0)-AmP-CPG which is heterogeneously supported on silica containing material.

2. The method according to claim 1, wherein the reducing agents are ammonium formate and formic acid, and wherein the solvent is toluene.

3. The method according to claim 1, wherein the reduction is carried out at a temperature of 20-80° C.

4. The method according to claim 1, wherein the alcohol is converted to an aldehyde in step i), wherein the conversion of the alcohol to an aldehyde is conducted in the presence of NaOCl, TEMPO (2,2,6,6-tetramethylpiperidin-1-yl)oxyl), NaOH, KBr, and and $O_2$.

5. The method according to claim 4, wherein step i) comprises:
   i. adding a solution of KBr to a solution comprising the alcohol and TEMPO;
   ii. stirring the mixture;
   iii. adding NaOCl solution to the reaction mixture;
   iv. adding NaOH to the reaction mixture in the presences of $O_2$; and
   v. stirring the mixture.

6. The method according to claim 1, wherein the alcohol is converted to a ketone in step i), wherein the conversion of the alcohol to a ketone is conducted in the presence of $O_2$, TEMPO, $HNO_3$, and HCl.

7. The method according to claim 6, wherein step i) comprises:
   i. adding TEMPO to the alcohol in the presence of $O_2$;
   ii. adding a mixture of $HNO_3$ in acetonitrile;
   iii. adding a mixture of HCl in acetonitrile; and
   iv. optionally heating the mixture.

8. The method according to claim 1, wherein the alcohol is a diol, and wherein said diol is in step i) converted to an aldol which then undergoes a spontaneous catalytic retro-aldol reaction to the corresponding aldehyde moieties, and wherein the C=O bond of the aldehydes are subsequently reduced to a C—H bond in step iii).

9. The method according to claim 8, wherein the diol is selected from lignin or derivatives thereof.

10. The method according to claim 9, comprising:
    i. providing lignin and oxidizing the lignin to a polymer comprising aldehyde groups;
    ii. the polymer comprising aldehyde groups which have been provided in the previous step subsequently undergo spontaneous catalytic retra-aldol reaction which leads to a depolymerization; and
    iii. reducing the aldehyde groups.

11. The method according to claim 1, wherein the alcohol is a primary alcohol, and wherein the primary alcohol is converted to an aldehyde in step i), and wherein the C=O bond of the aldehyde is subsequently reduced to a C—H bond.

12. The method according to claim 1, wherein the alcohol is vanillyl alcohol and wherein vanillyl alcohol is converted to its respective aldehyde in step i), and wherein the C=O bond of the aldehyde is subsequently reduced to a C—H bond.

13. The method according to claim 1, wherein the alcohol is a secondary alcohol, and wherein said secondary alcohol is converted to a ketone in step i), and wherein the C=O bond of the ketone is subsequently reduced to a C—H bond.

14. A method of conversion of a C—O or C=O bond to a C—H bond, comprising:
    i. providing a compound comprising a C—O bond or a C=O bond, wherein said compound is selected from the group consisting of an aldehyde, a ketone, an alcohol, an aldol, a compound having an ether bond beta to a hydroxyl group, or a compound having an ether bond alpha to a carbonyl group; and ii. reducing the C—O or C═O bond to a C—H bond in a solvent comprising a reducing agent and a catalyst, wherein the catalyst is selected from the group consisting of a heterogeneous metal catalyst and homogeneous organometallic complex, wherein the catalyst is a Pd-catalyst selected from the group consisting of Pd(0)-AmP-MCF and Pd(0)-AmP-CPG, which is heterogeneously supported on silica containing material wherein the catalyst is a Pd-catalyst selected from the group consisting of Pd(0)-AmP-MCF and Pd(0)-AmP-CPG, wherein the homogeneous organometallic complex comprises Pd, Ir, Ru, Ni, Co, Cu complexes; and iii. wherein an optional step of providing an alcohol and then converting the alcohol to a compound comprising a C═O bond is provided before step i).

15. The method according to claim 14, wherein the reducing agent is selected from the group consisting of hydrogen, formic acid, and ammonium formate.

16. The method according to claim 14, wherein the reducing agent is ammonium formate and formic acid when the compound comprising a C—O bond is an alcohol.

17. The method according to claim 14, wherein the ammonium formate and formic acid are added in a ratio of 0.25 and 6.6, respectively, in relation to the alcohol, or in a ratio of 0.25 and 3.3, respectively, in relation to the alcohol.

18. The method according to claim 16, wherein the solvent is ethanol and/or water.

19. The method according to claim 14, wherein the reducing agents are ammonium formate and formic acid when the compound comprising a C═O bond is an aldehyde or ketone, and wherein the solvent is toluene.

20. The method according to claim 14, wherein the reduction is carried out at a temperature of 20-80° C.

21. The method according to claim 14, wherein a step of providing an alcohol and then converting the alcohol to a compound comprising a C═O bond is provided before step i), wherein said alcohol is a primary alcohol.

* * * * *